(12) United States Patent
Mishra

(10) Patent No.: US 12,062,417 B2
(45) Date of Patent: Aug. 13, 2024

(54) SYSTEM, METHOD AND COMPUTER ACCESSIBLE-MEDIUM FOR MULTIPLEXING BASE CALLING AND/OR ALIGNMENT

(71) Applicant: New York University, New York, NY (US)

(72) Inventor: Bhubaneswar Mishra, Great Neck, NY (US)

(73) Assignee: New York University, New York, NY (US)

( * ) Notice: Subject to any disclaimer, the term of this patent is extended or adjusted under 35 U.S.C. 154(b) by 927 days.

(21) Appl. No.: 16/865,076

(22) Filed: May 1, 2020

(65) Prior Publication Data

US 2020/0350037 A1 Nov. 5, 2020

Related U.S. Application Data

(60) Provisional application No. 62/841,437, filed on May 1, 2019.

(51) Int. Cl.
| | |
|---|---|
| *G01N 33/48* | (2006.01) |
| *G16B 30/10* | (2019.01) |
| *G16B 30/20* | (2019.01) |
| *G16B 35/20* | (2019.01) |

(52) U.S. Cl.
CPC .............. *G16B 35/20* (2019.02); *G16B 30/10* (2019.02); *G16B 30/20* (2019.02)

(58) Field of Classification Search
None
See application file for complete search history.

(56) References Cited

U.S. PATENT DOCUMENTS

| | | | |
|---|---|---|---|
| 7,232,656 B2 | 6/2007 | Balasubramanian et al. | |
| 2002/0055112 A1 | 5/2002 | Patil et al. | |
| 2004/0053246 A1 | 3/2004 | Sorenson | |
| 2005/0221341 A1 | 10/2005 | Shimkets et al. | |
| 2012/0116688 A1* | 5/2012 | Mishra ................... | G16B 30/10 702/20 |
| 2016/0080528 A1* | 3/2016 | Mishra ................... | G16B 30/00 713/168 |

OTHER PUBLICATIONS

International Search Report for PCT/US2010/032613 mailed Dec. 8, 2010.
International Written Opinion for PCT/US2010/032613 mailed Dec. 8, 2010.
B. Ewing et al., "Base-Calling of Automated Sequencer Traces Using Phred. I. Accuracy Assessment," Genome Research, vol. 8, pp. 175-185, 1998.
B. Ewing et al., "Base-Calling of Automated Sequencer Traces Using Phred. II. Error Probabilities," Genome Research, vol. 8, pp. 186-194, 1998.
Meller, A. et al., Rapid Nanopore Discrimination Between Single Polynucleotide Molecules, PNAS, vol. 97, No. 3, pp. 1079-1084, 2000.
The International HapMap Consortium, The International HapMap Project, Nature, vol. 426, No. 18, pp. 789-796, 2003.
The International HapMap Consortium, "A Haplotype Map of the Human Genome", Nature, vol. 437, No. 27, pp. 1299-1320, 2005.
M. Stephens and P. Donelly,"A Comparison of Bayesian Methods for Haplotype Reconstruction from Population Genotype Data" Am. J. of Hum. Genet., vol. 73;5, pp. 1162-1169, 2003.
L. Feuk et al., "Structural Variation in the Human Genome" Nature Review Genetics, vol. 7, No. 2, pp. 85-97, 2006.
J.Sebat et al. "Large-Scale Copy Number Polymorphism in the Human Genome" Science, vol. 305, No. 5683, pp. 525-528, 2004.
Efron, B., "Large-scale simultaneous hypothesis testing: the choice of a null hypothesis" J. Am. Statist. Assoc., vol. 99, pp. 96-104, 2004.
Nyren, P. et al. "Solid Phase DNA minisequencing by an Enzymatic Luminometric Inorganic Pyrophosphate Detection Assay" Annal. Biochem. vol. 208;1, pp. 171-175; 1993.
Ronaghi, M. et al. "PCR-Introduced Loop Structure as Primer in DNA sequencing" Biotechniques, vol. 25;5, pp. 876-884, 1998.
Margulies, M. et al."Genome Sequencing in Micro-fabricated High-Density Picaoliter Reactors" Nature, vol. 437;15, pp. 376-380, 2005.
Erlich Y., et al. "Alta-Cyclic: a self-optimizing base caller for next-generation sequencing" Nature Methods, vol. 5; 8, pp. 679-682, 2008.
Barany, F. "The Ligase Chain Reaction in a PCR World" PCR Methods Applications., vol. 1;5 pp. 5-16, 1991.
Nickerson, D.A., et al. "Automated DNA Diagnostics Using an ELISA-Based Oligonucleotide Ligation Assay" PNAS, vol. 87; 22, pp. 8923-8927, 1991.
Drmanac, R., et al. "DNA Sequence Determination by Hybridization: A Strategy for Efficient Large-Scale Sequencing" Science, vol. 260; pp. 1649-1652, 1993.
Broude, N.E., et al. "Enhanced DNA Sequencing by Hybridization" PNAS, vol. 91; 8, p. 3072-3076, 1994.
Evene, M.J., et al. "Zero-Mode Waveguides for Single-Molecule Analysis at High Concentrations" Science, vol. 299, pp. 682-686 2003.

(Continued)

*Primary Examiner* — Anna Skibinsky
(74) *Attorney, Agent, or Firm* — HUNTON ANDREWS KURTH LLP

(57) ABSTRACT

An exemplary system, method and computer-accessible medium for multiplexing base-calling of a plurality of nucleic acid molecules in the same flow cell is provided. When multiplexing for just two nucleic acid molecules, it can operate by selecting a first base call for a first nucleic acid molecule and a second base call for a second nucleic acid molecule, after having placed them in the same flow cell and obtaining the combined raw intensity output. It can use as prior the appropriate reference genome sequences from which the nucleic acid molecules can be derived in order to create a score function, which can additionally be constrained by various penalty functions. It can derive accuracy and speed by using a branch and bound strategy as well as by performing alignment and base-calling in one step per cycle.

20 Claims, 14 Drawing Sheets

(56) References Cited

OTHER PUBLICATIONS

Fologea, D. et al. "Detecting Single Stranded DNA with a Solid State Nanopore" Nano Letters, vol. 5, No. 10, pp. 1905-1909, 2005.
Ilumina, Inc. Genome Analyzer IIx System Specification. 2009.
Kircher, M. & Kelso, J. High-throughput DNA sequencing-concepts and limitations. Bio Essays 32, 524-36 (2010).
Loman, N. J. et al. Performance comparison of benchtop high-throughput sequencing platforms. Nature Biotechnology 30, 434-439 (2012).
Metzker, M. L. Sequencing technologies—the next generation. Nature Reviews Genetics 11, 31-46 (2010).
Niedringhaus, T. P., Milanova, D., Kerby, M. B., Snyder, M. P. & Barron, A. E. Landscape of next-generation sequencing technologies. Analytical Chemistry 83, 4327-4341 (2011).
Shendure, J. & Ji, H. Next-generation DNA sequencing. Nature Biotechnology 26, 1135-1145 (2008).
Chevreux, B., Pfisterer, T. & Suhai, S. Automatic Assembly and Editing of Genomic Data. in Genomics and Proteomics: Functional and Computational Aspects 51-65 (Kluwer Academic Publishers, 2000).
Ilumina, Inc. Genome Analyzer Pipeline Software User Guide. (2008).
Smith, A. D., Xuan, Z. & Zhang, M. Q. Using quality scores and longer reads improves accuracy of Solexa read mapping. BMC Bioinformatics 9, 128:1-8 (2008).
Stephens, M., Sloan, J. S., Robertson, P. D., Scheet, P. & Nickerson, D. A. Automating sequence-based detection and genotyping of SNPs from diploid samples. Nature Genetics 38, 375-381 (2006).
Rougemont, J. et al. Probabilistic base calling of Solexa sequencing data. BMC Bioinformatics 9, 431 :1-12 (2008).
Li, R., Li, Y., Kristiansen, K. & Wang, J. Soap: short oligonucleotide alignment program. Bioinformatics 24, 713-714 (2008).
Sundquist, A., Ronaghi, M., Tang, H., Pevzner, P. & Batzoglou, S. Whole-genome sequencing and assembly with highthroughput, short-read technologies. PLoS One 2, e484 (2007).
Chevreux, B. et al. Using the miraEST assembler for reliable and automated mRNA transcript assembly and SNP detection in sequenced ESTs. Genome Res. 14, 1147-1159 (2004).
Gordon, D., Abajian, C. & Green, P. Consed: A Graphical Tool for Sequence Finishing. Genome Res. 8, 195-202 (1998).
Luque, G. & Alba, E. Metaheuristics for the DNA Fragment Assembly Problem. Int. J. Comput. Intel I. Res. 1, 98-108 (2005).
Giddings, M. C., Brumley, R. L., Haker, M. & Smith, L. M. An adaptive, object oriented strategy for base calling in DNA sequence analysis. Nucleic Acids Research 21, 4530-4540 (1993).
Brockman, W. et al. Quality scores and SNP detection in sequencing-by-synthesis systems. Genome Research 18, 763-770 (2008).
Delcher, A. L. et al. Alignment of whole genomes. Nucleic Acids Research 27, 2369-2376 (1999).
Hillier, L. W. et al. Whole-genome sequencing and variant discovery in C. elegans. Nature Methods 5, 183-188 (2008).
Horton, P. A branch and bound algorithm for local multiple alignment. Pacific Symposium on Biocomputing 368-383 (1996).
Li, H., Ruan, J. & Durbin, R. Mapping short DNA sequencing reads and calling variants using mapping quality scores. Genome Research 18, 1851-1858 (2008).
Marth, G. T. et al. A general approach to single-nucleotide polymorphism discovery. Nature Genetics 23, 452-456 (1999).
Ossowski, S. et al. Sequencing of natural strains of *Arabidopsis thaliana* with short reads. Genome Research 18, 2024-2033 (2008).
Salzberg, S. L., Church, D., DiCuccio, M., Yaschenko, E. & Ostell, J. The genome Assembly Archive: a new public resource. PLoS Biology 2, E285:1273-1275 (2004).
Schatz, M. C., Phillippy, A. M., Shneiderman, B. & Salzberg, S. L. Hawkeye: an interactive visual analytics tool for genome assemblies. Genome Biology 8, R34:1-12 (2007).
Schmid, K. J. et al. Large-scale identification and analysis of genome-wide single-nucleotide polymorphisms for mapping in *Arabidopsis thaliana*. Genome Research 13, 1250-1257 (2003).
Smith, D. R. et al. Rapid whole-genome mutational profiling using next-generation sequencing technologies. Genome Research 18, 1638-1642 (2008).

* cited by examiner

SYSTEM, METHOD AND COMPUTER ACCESSIBLE-MEDIUM FOR MULTIPLEXING BASE CALLING AND/OR ALIGNMENT

CROSS-REFERENCE TO RELATED APPLICATION(S)

This application relates to and claims priority from U.S. Patent Application No. 62/841,437, filed on May 1, 2019, the entire disclosure of which is incorporated herein by reference. This application also relates to U.S. Patent Publication No. 2012/0116688, the entire disclosure of which is incorporated by reference.

FIELD OF THE DISCLOSURE

The present disclosure relates generally to exemplary embodiments of systems, methods, and computer-accessible mediums for base calling and alignment, and more specifically to exemplary embodiments of system, method and computer accessible-medium for multiplexing base calling and alignment.

BACKGROUND INFORMATION

Currently, there are efforts to develop a relatively inexpensive genome sequencing platform that can be of acceptable accuracy (e.g., about one base error in 100 to 1,000 base pairs ("bps")) and relatively high-speed (e.g., a turn-around/processing time of less than an hour to twenty four hours). However, current sequencing platforms are generally limited to sequencing a single deoxyribonucleic acid (DNA) molecule per flow cell at a time. Thus, in order to increase output of sequencing machines, the speed for each genome sequencing has to be increased. Another option can be to increase the number of DNA molecules per flow cell that can be sequenced at a time.

Thus, it may be beneficial to provide an exemplary system, method and computer accessible-medium for multiplexing base calling and alignment, which can overcome at least some of the deficiencies described herein above.

SUMMARY OF EXEMPLARY EMBODIMENTS

To that end, an exemplary system, method and computer-accessible medium for selecting a first base call for a first nucleic acid molecule and a second base call for a second nucleic acid molecule can be provided, which can include, for example, obtaining a combined raw intensity output derived from the first nucleic acid molecule and the second nucleic acid molecule. For example, the first nucleic acid molecule can be in a same flow cell as the second nucleic acid molecule. A reference sequence(s) can be obtained for a genome related the first and second nucleic acid molecules. A score function can be optimized, subject to a constraint(s), based on a plurality of intensities and the reference sequence(s). The optimized score function can be applied to the combined raw intensity output. The combined raw intensity output can be mapped to a set of possible alignments, the reference sequence(s) and a set of possible base calls. Further the first base call and the second base call can be selected from the set of possible base calls.

In some exemplary embodiments of the present disclosure, the combined raw intensity output can include raw intensity outputs received simultaneously from the first and second nucleic acid molecules. The combined raw intensity output can include a first raw intensity output received from the first nucleic acid molecule at a first time and a second raw intensity output received from the second nucleic acid molecule at a second time, where the second time can be later than the first time. The first nucleic acid molecule can be the same as, or different than, the second nucleic acid molecule. The constraint(s) can include a penalty function(S).

In certain exemplary embodiments of the present disclosure, the combined raw intensity output can be generated by introducing a plurality of primers at different cycles in a Sequencing-By-Synthesis process. The reference sequence(s) can be obtained independently from the combined raw intensity output. The set of possible base call can include a first set of possible base calls and a second set of possible base calls, and the combined raw intensity output can be mapped to the first set of possible base calls for the first nucleic acid molecule and to the second set of possible base calls for the second nucleic acid molecule.

In some exemplary embodiments of the present disclosure, the first and second nucleic acid molecules deoxyribonucleic acid molecules. In certain exemplary embodiments of the present disclosure, the first and second nucleic acid molecules are ribonucleic acid molecules. The reference sequence(s) can include a single reference sequence related to first and second nucleic acid molecules. The reference sequence(s) can include two references, where one of the reference sequence can be related to the first nucleic acid molecule and another of the reference sequences can be related to the second nucleic acid molecule. The combined raw intensity can be obtained from a single channel on a nucleic acid sequencing machine.

In certain exemplary embodiments of the present disclosure, a first raw intensity output of the combined raw intensity output can be obtained from a first channel on a nucleic acid sequencing machine and a second raw intensity output of the combined raw intensity output can be obtained from a second channel on the nucleic acid sequencing machine, where the first channel is different than the second channel. The combined raw intensity output can include a first raw intensity output from the first nucleic acid molecule received simultaneously with a second raw intensity output from the second nucleic acid molecule. The first and second nucleic acid molecules can be from a virus(es). The first and second nucleic acid molecules can be placed on a single flow cell and the single flow cell can be inserted into a nucleic acid sequencing machine.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figure(s) showing illustrative embodiment(s) of the present disclosure, in which.

Figure 1A:
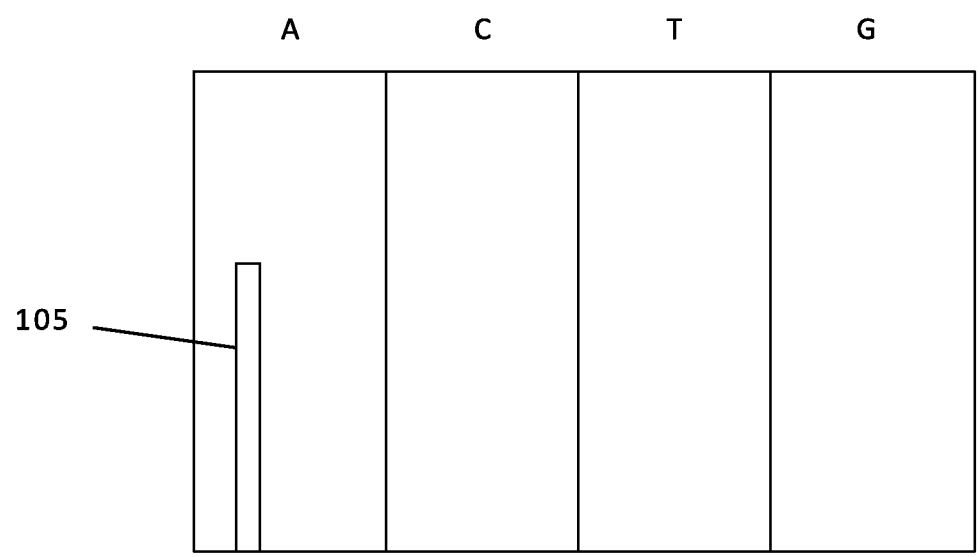
FIGS. 1A-1C are exemplary diagrams illustrating intensity spikes in specific channels according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method and computer-accessible medium, according to an exemplary embodiment of the present disclosure can read a plurality of nucleic acid molecules, e.g., DNA or ribonucleic acid (RNA) molecules, which can be contained in a single flow cell, simultaneously using a multiplexed-mode. The plurality of multiplexed molecules can come from different regions (e.g., overlapping or non-overlapping) on the same chromosome, in addition to being from two or more different molecules of unrelated origin. The exemplary multiplexed mode can be (i) synchronized or it can be (ii) staggered. The nuclei acid molecules can be from viruses, bacteria, or any other organism (e.g., human DNA).

The exemplary system, method and computer-accessible medium, according to an exemplary embodiment of the present disclosure, can interpret the intensity data generated simultaneously by two nucleic acid molecules both initiated to start with their respective first bases. The multiple channels in a sequencing machine can be leveraged to receive multiple intensities related to the multiple samples. When a read is performed, multiple intensity values will be received, one for each sample. The intensity values can be convolved, using any suitable procedure or method as described below, to determine the corresponding intensity value for each sample. The genome can then be assembled as discussed herein. For example, if only one strong intensity value is received, then using a suitable assembly procedure as discussed herein, and based on a known reference sequence, the intensity value can be assigned to a specific channel (e.g., the A channel). If multiple strong intensity values can be received, the reference sequence can be leveraged to determine which sample corresponds to which intensity.

Figure 1B:
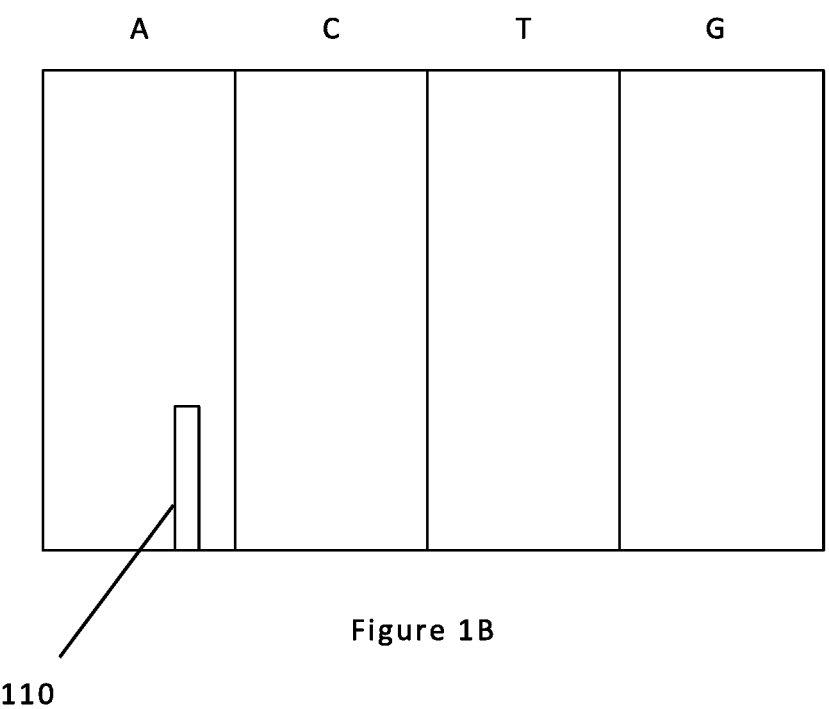
Figure 1C:
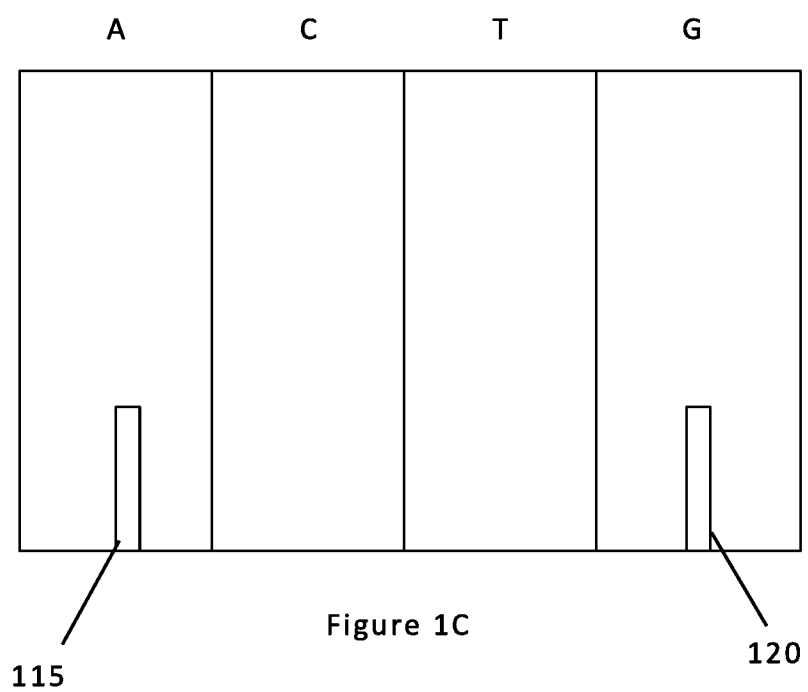

FIGS. 1A-1C show exemplary diagrams illustrating intensity spikes in specific channels according to an exemplary embodiment of the present disclosure. For illustrative purposes only, FIGS. 1A-1C are shown as having no noise such that a determination can be made as to the appropriate channel where the intensity spike has occurred. However, as described herein, the intensity spike can be noisy. Thus, various suitable exemplary procedures (e.g., Totalrecaller, Hidden Markov model, etc. as discussed herein) can be used to determine the appropriate channel based on the noise.

For example, as shown in FIGS. 1A and 1B, a single intensity spike is observed in the A channel for a single read for multiple genomes (e.g., in this case two genomes). Since only a single spike is observed, the exemplary system, method and computer-accessible medium can determine that the spike is applicable to both genomes. The intensity value can be additive. Thus, as shown in FIG. 1A, the combined intensity value 105 can be an additive combination of two lower intensity values separately produced by the read from each genome. However, as shown in FIG. 1B, the combined intensity value 110 does not have to be additive, or may not be significantly additive. In such an exemplary case, the absence of an intensity spike on a different channel (e.g., on the C, T, or G channels) is an indication that the read for both genomes is on the A channel. Additional reads can be performed, and as long as the intensity values are observed on the same channel, then the read can be associated with both genomes.

FIG. 1C shows an exemplary case in which two intensity spikes are observed on two channels (e.g., A and G). Specifically, intensity spike 115 is observed on the A channel and intensity spike 120 is observed on the G channel. In such exemplary case, it is not readily apparent which intensity spike corresponds to the read from each genome. In order to address this, the reference sequence associated with each genome can be leveraged. Each genome can have its own associated reference sequence. The exemplary system, method and computer-accessible medium, according to an exemplary embodiment of the present disclosure, can determine the next read in the reference sequence and match it to one of the observed intensity spikes (e.g., either intensity spike 115 or intensity spike 120). Based on the reference sequence, the intensity spikes can be associated with the particular genome. The exemplary system, method and computer-accessible medium can continue to assemble the genome regardless of whether or not the observed intensity is on the same channel (e.g., as shown in FIGS. 1A and 1B) or on different channels (e.g., as shown in Figure C).

If both of the reads deviate from the reference sequence associated with the genome, a low score can be produced, and an inconsistency can be detected. This can result in an equivocal result, or a result with a low statistical confidence. This information can be taken into account during any pruning procedure performed by the exemplary system, method and computer-accessible medium.

When noise is observed in the read intensities, the exemplary system, method and computer-accessible medium can utilize an exemplary procedure (e.g., a TotalRecaller ("TRC")) procedure, where a path in the tree can be scored by the formula in which the score function has two components: one that can determine whether the path can be consistent with the intensities observed from one of the nucleic acid molecules (e.g., with a noise component due to the interference from the second nucleic acid molecules) and vice versa, and a second component based on the alignment to the reference of the sequence from the path in the tree. A single reference sequence can be used for each of the multiple samples, or each sample can have its own reference sequence. Various combinations of reference sequences can be used based on the number of sampled. Additionally, various other exemplary suitable procedures can be used for assembling the sequence (e.g., a Hidden Markov model, Bayesian prior, Stringomics, statistical models, FM index, raw sequences, compressed forms of raw sequences, etc.). Because there can be two or more nucleic acid molecules, two or more high-scoring paths can be expected, which can explain the data from the perspectives of the chemistry of the platform, as well as the known reference sequence. Thus, a pair of paths (or more than two paths) can be generated, which when overlapped, can be consistent with observed intensity-pairs as well as two different substrings of the exemplary reference.

Additional constraints represented by a penalty function for a path can be added, depending on what fraction of its bases cannot be explained by simple overlap with a well-scoring path (e.g., a path with a score above a threshold). Exemplary constraints can include, but are not limited to, the degree of multiplexing, offsets for multiplexing, reference sequences, and noise statistics) Additional generalization to more than two molecules can be performed (e.g., mutatis mutandis) and should be apparent to a person having ordinary skills in the art.

The exemplary system, method and computer-accessible medium, according to an exemplary embodiment of the present disclosure, can also stagger the genome sequencing (e.g., the exemplary TotalRecaller procedure can be used to interpret the intensity data generated simultaneously by two or more nucleic acid molecules, but one of them can be initiated with its first base before the other). For example, the initiation of the sequences can be staggered by sequentially introducing the primers at different cycles in the Sequencing-By-Synthesis process, or potentially via an optically/electrochemically activated de-blocking chemistry. The degree of staggering can be platform dependent and can be determined empirically. Examples of degrees of staggering can be in the range of about 10 to about 60 bases. The exemplary procedure can effectuate this case in a manner similar to the one described above, but can take into account the fact that at the beginning, the complexity of the data can be low, and the first molecule can be well-anchored to a region of the reference, before the interference from the second molecule can increase the complexity of the data. Symmetrically, since, by the time the data from the second molecule arrives, the first molecule would have had an interpretation with significantly less ambiguity, the pruning by branch-and-bound can be performed with significantly less ambiguity and complexity.

The exemplary system, method and computer-accessible medium, according to an exemplary embodiment of the present disclosure, can implement the synchronized or staggered multiplexing in conjunction with barcodes, where the selected barcodes can be endowed with some error correcting properties (e.g., pairwise hamming distance exceeds a threshold) or can be attached at the beginning of the nucleic acid molecules with linkers of varying lengths. Thus, the multiplexed barcoded nucleic acids can be sequenced as above using an exemplary procedure, but with additional constrains on the scores. For example, if a pair of nucleic acid molecules can be multiplexed sequenced, then a pair of high-scoring paths together can explain the observed data as well as the constrains imposed to achieve error-correcting coding; similarly for a population exceeding two nucleic acid molecules.

The exemplary system, method and computer-accessible medium, according to an exemplary embodiment of the present disclosure, can also be used to determine if a virus or bacteria (e.g., a particular virus or a bacteria) is present in the multiple samples. For example, it might not be known whether or not a person is infected with a virus of a bacteria. Thus, the exemplary system, method and computer-accessible medium can be used not only to sequence a particular virus or bacteria, but also to determine whether or not the virus or bacteria is even present in the sample.

Figure 2:
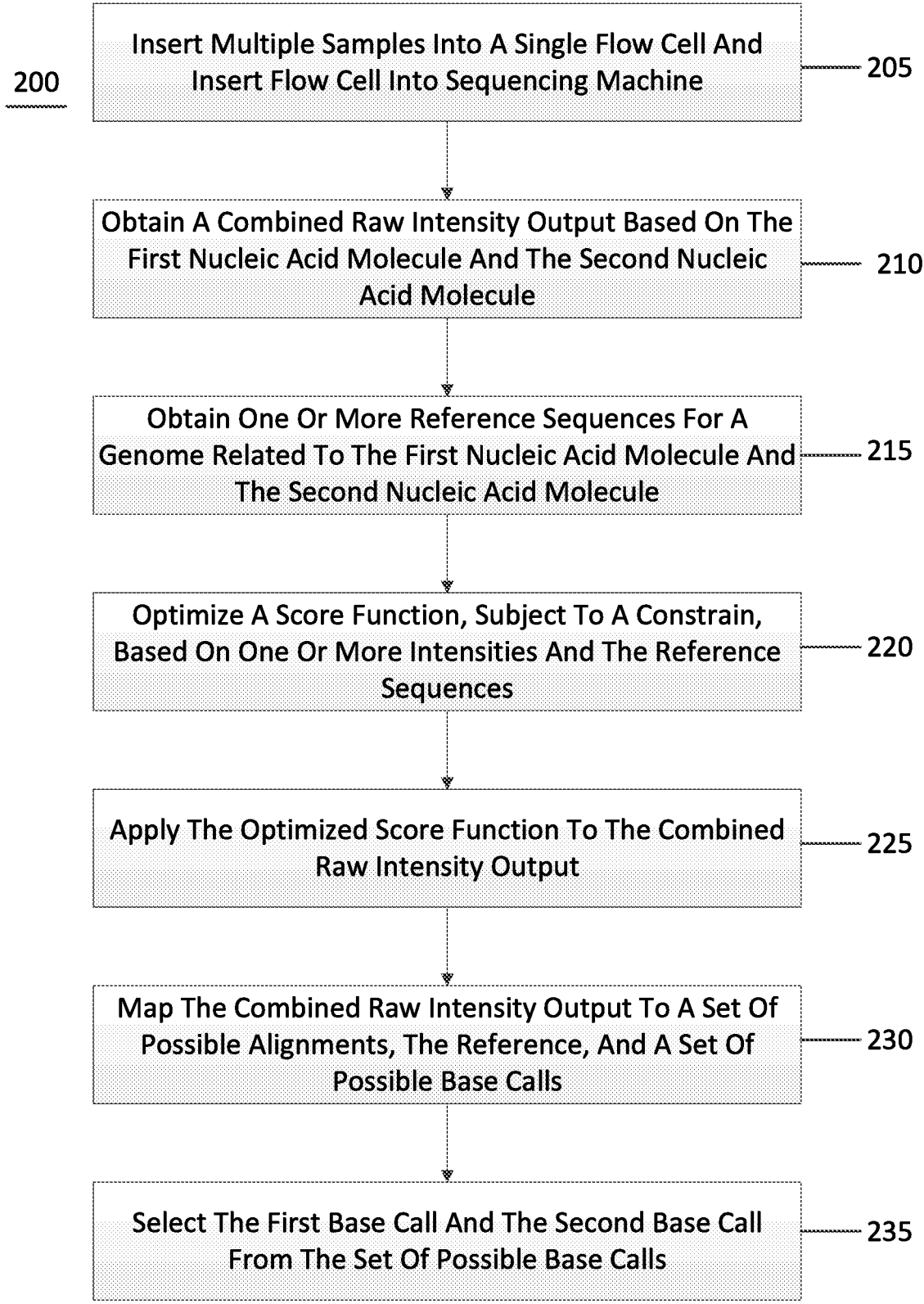
FIG. 2 is an exemplary diagram of an exemplary method for selecting a first base call for first genome and a second base call for a second genome according to an exemplary embodiment of the present disclosure.

FIG. 2 illustrates an exemplary flow diagram of an exemplary method 200 for selecting a first base call for first nucleic acid molecule and a second base call for a second nucleic acid molecule according to an exemplary embodiment of the present disclosure. For example, at procedure 205, multiple genomic samples can be inserted into a single flow cell, and then inserted into a sequencing machine. At procedure 210, a combined raw intensity output can be obtained that can be based on a first and second nucleic acid molecules. At procedure 215, one or more reference sequences for genomes related the first and second nucleic acid molecules can be obtained. For example, a single reference sequence can be obtained if the genome is the same for the first and second nucleic acid molecules, or multiple reference sequences can be obtained if the first and second nucleic acid molecules are associated with different genomes. The number of reference sequences can be based on the number of nucleic acid molecules (e.g., there can be more than two nucleic acid molecules, and more than two genomes).

At procedure 220, a score function, subject to at least one constraint, can be optimized based on a plurality of intensities and the reference sequences. At procedure 225, the optimized score function can be applied to the combined raw intensity output in order to deconvolve the raw intensity values. At procedure 230, the combined raw intensity output can be mapped to a set of possible alignments, the reference and a set of possible base calls. At procedure 235, the first base call and the second base call can be selected from the set of possible base calls. An exemplary embodiment of a score function/procedure used to deconvolve the raw intensity values is described herein below.

For example, various exemplary embodiments in accordance with the present disclosure can address bioinformatics problems described herein above to be solved in order to handle the data from certain available sequencing technologies. Further, various exemplary embodiments in accordance with the present disclosure can also be useful to anticipate potential future needs by creating a general probabilistic framework that can be helpful to provide an exemplary architecture of methods, procedures, computer-accessible medium and systems that can utilize data from future sequencing platforms.

In accordance with certain exemplary embodiments of the present disclosure, it is possible to address the issues described herein above by, e.g., providing exemplary rigorous common probabilistic frameworks, which (with parametric tailoring) can be applicable to various platforms, by formulating the structure of basic bioinformatics problem modules in terms of global optimization specifications, and by solving them using efficient statistical procedures, whose computational complexity could be tamed through score-based branch-and-bound implementations. Exemplary embodiments in accordance with the present disclosure can indicate how to avoid dependence on greedy heuristics that myopically trade-off global optimality for computational efficiency.

Certain exemplary embodiments according to the present disclosure can be used to determine and utilize a probabilistic extension and alignment of ultra-short (e.g., 30-60 bps) sequence-read data, which data can be deficient due to, e.g., a loss of synchronization in addition to other deficiencies described herein. Such data can be associated with certain available and/or anticipated sequencing technologies (e.g., Solexa, etc.), whereas such exemplary class of technology can be referred to as "Short Read Sequence Extension and Alignment".

For example, according to certain exemplary embodiments of the present disclosure, parametric and/or non-parametric score function(s) can be used in a branch-and-bound-based exhaustive search approach to efficiently solve various non-convex optimization problems appearing in the exemplary procedures used to solve base-calling for a wide class of nucleic acid sequencing platforms, align the raw reads directly to any given nucleic acid sequence (e.g., a reference sequence), and use the data to detect (directly or indirectly) a wide class of polymorphisms (e.g., SNPs, CNVs, indels, SVs, etc.) Accordingly, certain exemplary methods, computer-accessible medium, and systems are described herein for base-calling, resequencing, aligning, polymorphism detection, etc. using data obtained directly from various sequencing platforms, known haplotypic or genotypic reference sequences and databases of polymorphisms. These exemplary methods, procedures, computer-accessible medium, and systems can provide important strategies that may be used for statistically combining disparate genomic information from more than one genomic sample, simultaneously, and exemplary embodiments of chemical protocols can be utilized which may, e.g., in parallel, manipulate and interrogate a large amount of genomic, sequencing, polymorphism, and disease association data in various environments (e.g., personalized medicine, population studies, clinical studies, pharmacogenomics, etc.).

In addition, exemplary embodiments of methods, procedures, computer-accessible medium, and systems for base-calling, alignment, and polymorphism detection are provided herein. Certain exemplary applications of such exemplary methods, procedures, computer-accessible medium and systems according to the present disclosure can include, e.g., analyzing patient genomes to predict susceptibility to various genetic or genomic diseases, or analyzing patient genomes to diagnose genomic instability and mutations as the basis of cancer. Exemplary embodiments according to the present disclosure can also have agricultural and/or biomedical applications in drug and/or vaccine discovery and applications, through understanding the behavior of a cell in an altered state (e.g., cancer, neuron-degeneration, auto-immune disease, etc.) genetically modifying a natural wildtype organism, genetic engineering, etc. Exemplary applications also can include, e.g., understanding population dynamics, neural behavior, evolutionary processes, genome evolution and aging, for example.

Exemplary embodiments of methods, procedures, computer-accessible medium, and systems according to the present disclosure can be provided that can comprise and/or be configured to obtain raw output from more than one genomic sample, simultaneously, that can include short-sequence reads from one or more sequencing platforms, while the choice of platform(s) to be selected can be based on user-preference and/or other criteria. It is possible to obtain one or more reference sequences, and interpret the raw-output data from multiple genomic samples, and align the short sequences to reference sequence(s), which can be performed in one integrated subprocess or in two separate subprocesses, to detect various polymorphisms.

Using certain exemplary embodiments in accordance with the present disclosure, it is possible to compute or determine one or more of most plausible solution(s) by searching the hypotheses space with a score function, which can be built out of (e.g., computed, processed, calculated, determined, derived, etc.) a log-likelihood function (e.g., from a parameterized model as done earlier). According to certain exemplary embodiments of the present disclosure, exemplary penalty (and/or score) function(s) can be determined and/or used that can relatively quickly recognize hypotheses that would unlikely be as true. For example, an exemplary good (e.g., preferred, beneficial, etc.) penalty and/or score function of this nature can include read-length-dependent upper and lower bounds determined so that unlikely solutions can be readily identified as they are scored (with a relatively very high probability) outside of the ranges defined.

It is possible to perform global optimization (or near optimization) by searching the hypotheses space potentially exhaustively (or near exhaustively) utilizing an intelligent pruning procedure using exemplary branch-and-bound heuristics. For example, the search tree can be a pruned quaternary tree (e.g., branching factor=4), where each node in position j can be expanded to the (j+1) position by augmenting the path with the base A, T, C, and G, and scoring a new resulting path for the hypothesis that it could have generated the data, which, in reality, can be obtained from the sequencing platform. If the score for a new node is below the desired range, the node can be pruned. In a more aggressive approach, it can be possible to utilize an exemplary embodiment using beam-search heuristics, where at any point only a fixed number (e.g., k=20) of the best possible hypotheses can be allowed to survive pruning and be included.

With a good (e.g., preferred, beneficial, etc.) exemplary parameterized model and the ability to compute an exemplary score analytically, the pruning procedure can be further simplified. For example, if the score function is linear and/or obeys the principle of optimality, it is possible to use exemplary tools such as those described by dynamic programming procedures. For certain score functions which can have a stringent local structure, the exemplary procedure can be implemented in such a way that it can utilize a greedy algorithm/procedure, dynamic programming algorithm/procedure, and/or graph search algorithm/procedure.

In addition, certain exemplary embodiments according to the present disclosure can provide a situation where it may not be possible to have a score function with preferred qualities and/or characteristics, or to derive such exemplary qualities from an understanding of the underlying physical and chemical processes (e.g., the polymerase chemistry can be highly base-specific or lead to stuttering in a way that cannot be fully understood). In such cases, it is possible to generate a non-parametric model according to certain exemplary embodiments of the present disclosure where a database containing a large number of observed base-calling of known sequence reads can be used to model the likelihood that a given hypothetical sequence of bases could have generated a particular data set, and thus to generate an exemplary score (and/or penalty) function, such as of the kind described hereinabove, for example. Such exemplary approach (procedure, method, technique, etc.) can be used to generate an exemplary tree with paths that can provide many plausible hypothetical solutions, which can be sorted by the exemplary score values, for example.

The members of an exemplary ordered collection of solutions, as can be produced or generated by exemplary embodiments in accordance with the present disclosure, can be further assigned an exemplary empirical p-value and used to, e.g., control false discovery rates. The generality and/or flexibility of an exemplary procedure in accordance with the present disclosure can be derived from its formulation of the problem in terms of global optimization, and its relatively efficient implementation using an exemplary branch-and-bound process. As the technology platform changes, exemplary embodiments in accordance with the present disclosure can be adapted to the newer platform or change to another platform by modifying the score function and/or by searching over different databases, for example.

Another advantage of certain exemplary embodiments according to the present disclosure can be with respect to how they can be integrated (e.g., interfaced, connected, etc.) with higher-level procedures and/or processes. For example, the problem of directly aligning a read from a sequencing platform (e.g., Solexa) with a particular segment of an organism's putative reference genome can be described as follows. Traditionally, the problem can be attempted to be solved by first executing a base-calling routine (e.g., Alta-Cyclic) on the data, and then using the output of this routine to perform a sequence alignment (e.g., BLAST, Smith-Waterman, SWAT, Neelernan-Wunsch, NEEDLE, etc.). Nonetheless, according to certain exemplary embodiments of the present disclosure, an exemplary tree-search with branch-bound procedure can be used that can combine two or more factors in its score. For example, one factor can represent how good of a match there is to the genomic segment (e.g., the edit-distance from the genomic segment). Another factor can represent how likely it is to have generated the observed data. The exemplary factors can be further revised based on the number of genomic samples being analyzed.

Exemplary embodiments according to the present disclosure can be implemented in terms of (a) hexanary trees with branching for 6 possibilities, e.g., match-A, match-T, match-C, match-G, insert-nucleotide and delete-nucleotide, and (b) evaluation with respect to an edit transcript as opposed to a sequence. Additional generalizations respecting other higher level algorithmic/procedural problems can include, e.g., SNP-calling, overlap detection, layout-generation, consensus sequence generation, shotgun or map-based assembly, as one having ordinary skill in the art should appreciate in light of the teachings provided herein.

Based on these general schemes, exemplary embodiments in accordance with the present disclosure can also adapt these such procedures to SNP calling and CNV detection.

For the SNP calling, certain exemplary embodiments according to the present disclosure can be used to extend the length of the sequence reads by running the base-calling routine for longer read lengths and keeping track of many plausible solutions with each base of the output reads (as well as the whole read) which can be scored as described herein above, for example. Since exemplary embodiments according to the present disclosure can obtain multiple alignments with appropriate base-calling and base-scoring, which can be based on the number of genomic samples, it is possible to convert the data into a SNP-calling score that can evaluate any particular base to be a single-nucleotide polymorphism, for example. By using an empirical-Bayes method for false-discovery rate control (see, e.g., Efron, B., *Large-scale simultaneous hypothesis testing: the choice of a null hypothesis, J. Am. Statist. Assoc.*, 99, 96-104 (2004)), exemplary embodiments according to the present disclosure can generate an empirical null model, which can distinguish true SNPs from false-positive ones. By further combining such data with the available HAPMAP database, it is possible to further distinguish detection of already known SNPS from novel SNPS.

One having ordinary skill in the art will appreciate in light of the teachings described herein various other benefits of exemplary embodiments of the present disclosure in areas of intelligent experimental design. For example, such benefits can be useful in a design a SNP calling procedure that can combine unequal coverage of reads from multiple platforms, e.g., shallow coverage of 454 sequence reads with a deeper coverage Solexa reads. In one such example, it is possible to determine that the 454 sequence reads have a longer length (e.g., about 700 bps to about 1000 bps), although cannot always be ideal or preferred for detection of novel SNPs because its homo-polymer errors can obfuscate the data. Nonetheless, these exemplary reads can provide a better indication of which SNPs of a particular haplotype from a haplotype block are being selected, and thus can help in resolving the multiple alignment problems for Solexa reads. However, by selecting the coverages for each kind of reads, base-calling parameters, read lengths, etc. it is possible to achieve designs best (or/and preferably) suited for accurate (or reasonably accurate, sufficiently accurate, etc.) SNP detection. While it is possible for a rough approximation of these parameters to be calculated analytically using probabilistic analysis, exemplary embodiments in accordance with the present disclosure can select the most optimal values utilizing a large-scale genomic simulation that can use, e.g., realistic models of genomes, populations, population structure, the score function(s) used by the algorithm(s), the procedure(s) and/or the error model(s) for the sequencing platform(s).

Exemplary embodiments in accordance with the present disclosure can address the CNV detection problem by, e.g., building on the exemplary alignment algorithm and/or procedure module in a manner similarly to as described herein with respect to the SNP calling problem. However, structural variations can introduce breakpoints in a sequence read that possibly do not appear in the reference sequence. Thus, an exemplary alignment procedure in accordance with the present disclosure can search over the appropriate suffixes and prefixes. For this purpose, it is possible to break the reads from multiple genomic samples into a set of k-mers, which it can first use to detect their rough alignment to the genomes using, e.g., preprocessing and efficient data-structures such as suffix arrays, suffix trees or Burrows-Wheeler indexing, and others as one having ordinary skill in the art should appreciate in view of the teachings provided herein.

However, when the coverage is low, the statistical significance of copy-number estimation can become an important issue.

For example, this exemplary problem can be addressed by certain exemplary embodiments in accordance with the present disclosure using a suitable (preferred) choice of the parameters in experimental design, which can likely involve a hybrid technique and/or procedure that can involve shallow-coverage data of long reads (e.g., 454-instrument). This can facilitate a detection of the break-points and deep-coverage data of short reads (e.g., Solexa platform), which can help achieve a better estimation of copy number. This exemplary analysis can be further coupled to a low resolution CNV analysis with a local copy-number segmentation procedure. It can be assumed that the low resolution data can have been obtained using a low-complexity representation of the genome, which can be sequenced with short reads. Other variations, which one having ordinary skill in the art should appreciate in view of the teachings provided herein, can be handled with appropriate changes to the basic procedures. For example, in accordance with certain exemplary embodiments according to the present disclosure, the data from different sources (e.g., low-resolution segmentation, high resolution deep-coverage short reads, high resolution low-coverage short reads, etc.) can be algorithmically or procedurally combined to obtain a relatively accurate copy number estimation. Similarly to the SNP data, it can be possible that the most optimal design (e.g., implementation) can be achieved through a large-scale simulation.

As discussed herein, advances in genomic related technologies, such as the development of recent sequencing technologies, have likely created further opportunities for interpreting data from recent (e.g., next generation) sequencing platforms using a general probabilistic framework. The resulting interpretations can have various biomedical applications, such as, e.g., finding common variants in polymorphisms, performing association studies, identifying certain genes that can be commonly implicated in diseases, and elucidating many of the cellular pathways upon which they act. Certain exemplary embodiments according to the present disclosure can provide relatively robust, efficient, and inexpensive technologies that can be used for, e.g., base-calling, resequencing, sequence alignment and detection of polymorphisms. For example, exemplary embodiments of methods, procedures, computer-accessible medium and systems can be provided for, e.g., base-calling, alignment and polymorphism detection.

In comparison to conventional technologies which can utilize greedy (e.g., relatively complex) heuristics and/or idealized model based simplification with suboptimal accuracy, certain exemplary embodiments in accordance with the present disclosure can be provided which use a global search-method with branch-and-bound heuristics (or beam search) to contain the complexity to relatively lower levels. Further, certain exemplary embodiments in accordance with the present disclosure can be used to determine a globally optimal solution and thus achieve a relatively high level of accuracy. In order to achieve a high computational space and time efficiency, certain exemplary embodiments according to the present disclosure can, e.g., prune out branches and utilize a selected score function.

For example, accuracy and validity of base-calling (and subsequent and/or integrated applications) can depend upon the fidelity of the underlying models describing the "error processes" that can be involved in the generation of raw data from a sequencing platform and reflected in the score. An exemplary score function can combine a Bayesian likelihood obtained from prior distributions derived from an exemplary model and certain penalty functions corresponding to certain constrains, and can be based on multiple genomic samples.

Relatively simple but meaningful heuristic score functions and/or penalty functions can be utilized according to certain exemplary embodiments of the present disclosure. For example, such exemplary functions can be provided by a human expert, and/or learned from (e.g., based upon, derived from, etc.) data utilizing a known "machine learning" approach, and/or by empirical Bayes approaches that can derive priors directly from the data. It is possible to utilize an empirical-Bayes method to determine the statistics and thresholds (e.g., null-model, threshold, p-values, base- or sequence-quality), thereby making the system relatively independent to the underlying technology, while being able to mix-and-match certain technologies, for example. In addition to the score functions, based on certain modeled, learned or known models, it is possible to use any other additional information (e.g., reference sequence or polymorphism databases, etc.), which can sharpen the exemplary score function and make the exemplary procedure behave more efficiently.

Further, certain exemplary procedures according to the present disclosure can utilize different/varying technologies including those for which no known models of error processes exist. For example, there can be available two different kinds of sequence-reads with two different length parameters from two different technologies that can be subjected to two different classes of error processes. From the data itself, it is possible to create an exemplary empirical model based on their interactions, and then use the resulting statistical distributions in the score function.

Additionally, certain exemplary embodiments of the procedures according to the present disclosure can be tuned heuristically (e.g., size of a priority queue and/or width of the beam search used in the branch-and-bound) to obtain the best (preferred, optimal, etc.) computational complexity and resource consumptions as a function of specific error parameters and preferred accuracy. Such exemplary processes can automatically provide a way to utilize underlying 0-1 laws in these technologies, such as, e.g., a law that states that there can exist certain error parameter thresholds (for which error processes that the underlying platforms' chemistry is subject) below which the probability of obtaining all the alignments correctly can be close to zero, while above this threshold, the correct alignment probabilities can jump (e.g., rapidly/sharply increase) to one. Such laws can have significant implications for the design of the underlying and/or applications, choice of the component technologies, parameters used in the technologies, and/or in selecting the manner in which the exemplary procedure can explore the search space which can be vast.

Moreover, according to certain exemplary embodiments of the present disclosure, the exemplary procedure can parallelize in a relatively straight-forward manner. Multiple regions in the multiple genomic sequences can be explored simultaneously by different processors, with search trees starting with a small number of randomly selected initial seeds (e.g., sequence-reads from which a local assembly can be initiated).

For example, an exemplary embodiment of the procedure according to the present disclosure for base calling can be described relatively simply in terms of the following exemplary subprocesses (utilizing generalizations that should be apparent to one having ordinary skill in the art in light of the present disclosure):

a: Start with a single nucleotide base (e.g., A, T, C, G), which can be the root of an exemplary tree); and b: Generate a QUATERNARY Tree by, e.g., starting with an unexplored leaf node (labeled by a nucleotide base) with the best score-value, selecting all four possible nucleotide bases (e.g., A, T, C, G) to expand the node by making them its children and computing their scores, and repeating until the tree cannot be expanded any further.

The exemplary score function (and/or components thereof) can be built from (e.g., generated, derived from, based upon, etc.) the logarithm of intensity information from each base-read from the multiple genomic sequences and its variance-based weighting of squared deviations computed using a distribution of similar positional intensities stored in an exemplary database. The exemplary database can be generated from a set of calibrating examples, which can be learned using machine-learning techniques and/or from a parametric model. It is also possible for the set to be adaptively and/or repeatedly learned and/or updated from each successive application of the exemplary procedure.

Further, certain exemplary embodiments of a base-calling procedure according to the present disclosure can use a relatively simple score function, its relative performance and relative accuracy with respect to the score functions that can be obtained by vendor-provided software. Such exemplary embodiments according to the present disclosure can utilize data obtained from Solexa reads of the viral genome from phiX, e.g., a bacteriophage.

For example, certain exemplary procedures according to the present disclosure can be implemented as a set of modular components that can be hierarchically combined and built upon the facilities available in a modular open-source assembler ("AMOS"), which was developed by a consortium of institutions and research centers associated with the University of Maryland. To facilitate the interaction of various isolated components, AMOS can facilitate a central data repository where certain genomic objects (e.g., reads, inserts, overlaps, contigs, scaffolds, etc.) can be collected and indexed. Exemplary embodiments according to the present disclosure can extend such bank implementation to also provide for the storage of raw data from different sequencing platforms as well as whole genome reference sequences. Programs in the assembly pipeline can be suitably adapted to communicate among the modules using the exemplary bank as an intermediate storage space. Further, certain exemplary embodiments of the procedure according to the present disclosure can use an AMOS visual analytics tool (e.g., Hawkeye) for inspection and validation of the corresponding results, for example.

Further, certain exemplary embodiments in accordance with the present disclosure can address some of the problems and issues described above by ensuring that the underlying procedures scale to other hardware platforms (e.g., cluster computers, multi-core architecture, cloud computing, etc.), and software architecture (e.g., MPI architecture, its successors and related designs).

For example, it is possible to consider nature of the genome alignment problems as follows. First, it is possible to consider sequencing the genome of an individual at a reasonable coverage with sequencing platform, e.g., Solexa machine, providing about a hundred million reads each of length about 50, which reads can be referred to as $r_1$, $r_2$, ... $r_k$. Further, it is possible to assume that an arbitrary read, say $r_i$, can align to several chromosomal locations in a genotypic reference sequence. Each such alignment can then be interpreted as implying that the read ri can belong to certain haplotype blocks, e.g., $h_j$, which can be assumed to have already been characterized from an existing population study of SNPs. It is also possible to denote such an event by a 0-1 variable $A(r_i, h_j)=1$. For example, the information connecting the reads to the haplotype blocks can be represented by a 0-1 integer matrix, A, with the conditions that $A(r_i, h_j)=0$ or 1. A certain independent 0-1 variable $x_j=0$ or 1 can exist, such that $Ax=1$ (e.g., for all i, sum_over_j $A(r_i, h_j) x_j=1$) can be satisfied. It is possible to obtain a solution that can minimize the total number of independent variables $x_j$ that can assume the value of 1 (e.g., min sum_over_j $x_j$). Such formulation can yield an Integer Linear Programming ("ILP") problem, which in the general setting can be NP-complete and hence, for all practical purposes, intractable.

Various exemplary embodiments of the present disclosure can improve the base-calling procedure for the sequencing platform, e.g., Solexa or other platforms, and thus extend the sequence read-lengths to be above a predetermined threshold value, e.g. about 100 bps (with some base-calls being inferred probabilistically with the estimated probability of the call recorded) so that the longer sequence-reads can be aligned almost uniquely, which can thus simplify the combinatorial optimization problem, for example. It is also possible to utilize certain potentially more-beneficial design strategies that can distribute tasks to more than one sequencing and mapping platform as well as to those that can combine sequence alignment and base calling in a single unified exemplary framework.

For example, in considering a sequencing platform that can produce short-reads of length k (in an idealized case with no base-call and/or homopolymer errors for explanatory purposes), such short-reads can then be aligned to an idealized random genome of length G. It can be assumed that all of the sequence-reads together cover the genome by a coverage factor of c. Accordingly, the probability that all of the sequence reads have unique locational identities and that the alignment procedure can find all of them can be expressed as $\exp[-cG^2/(k4^k)]$. Thus, for a fixed genome, whose length is G, if the read length is smaller than a threshold of $[1/(\ln 4)][2 \ln G+\ln c+\ln(1/eps)]$, the probability can take a relatively small value (e.g., be relatively closer to 0).

Further, as this threshold is exceeded, the probability can sharply rise to a value that can be very close to 1 (e.g., 1−eps) and the exemplary procedure can become computationally tractable, although it still can involve utilizing certain preprocessing and data-structures such as suffix trees and Burrows-Wheeler indexing to devise acceptable heuristics. It is possible to utilize such 0-1 laws (e.g., computational phase transition) in certain biological implementations and applications to circumvent the intractable computational complexity, which can be a significant technique used in matching particular genomic applications to the least expensive available biotechnology, for example.

Additionally, certain exemplary embodiments of a procedure according to the present disclosure can be based on a succinct parametric model that can address the dominant noise factors described herein above.

For example, it is possible that the base-calling problem can be reduced to, e.g., finding the most plausible hypothesis regarding the structure of a nucleic acid sequence that can generate a particular data set being analyzed. If the underlying parameters of the model are known, then it is possible to describe the resulting likelihood (or log-likelihood) function that would score a hypothesized sequence as to its likelihood of generating a particular dataset. Thus, the computational function can then be to discover the most likely hypothesis quickly from an exponentially large search space, for example. For this particular problem formulation, the exemplary stochastic process can involve exponential distributions that can be governed by a relatively small number of parameters, e.g., lead, lag, fading, and cross-talk, which can be estimated using certain exemplary robust machine-learning procedures. There can be a maximum likelihood estimation ("MLE") formulation that can be solved using simplifying tools from linear-algebra which can optimize a score based on log-likelihood, for example. Thus, this estimation problem can have a reasonably efficient solution. This exemplary method and/or procedure can be implemented in the Alta-Cyclic system for Solexa base-calling. Such exemplary implementation can be effective and validate the exemplary model and the linear-algebraic formulation in terms of the log-likelihood score. For example, it is possible to extend accurate base-calls over read lengths of about 48 bps to about 78 bps, while producing mean error rates in SNP sites below about two percent.

It is also possible, according to an exemplary embodiment of the present disclosure, to utilize a random walk model which can be characterized by three parameters, e.g., block-removal probability, nucleotide misincorporation probability and template loss probability. When used in conjunction with a cross-talk matrix, it is possible to describe signal-distortion as a function of cycle. Thus, given a hypothesized DNA sequence of any length, the exemplary model can estimate the probability that a particular data set can be generated from such particular sequence.

To address some of the prior limitations described herein, certain exemplary embodiments in accordance with the present disclosure can prune most of the unnecessary computation in the early processing stages, and thus be able to operate faster when augmented with "smart" score-functions. For example, certain procedures in accordance with the exemplary embodiments of the present disclosure can be used to generate the best, second best, third best solution, etc. up to a desired bound, which can then be used to calculate p-values, generate a more robust maximum a posteriori ("MAP") estimator, use Empirical-Bayes methods to create an empirical null model, control the false discovery rate, etc. Additionally, according to certain exemplary embodiments of the present disclosure, it is possible to circumvent some of the problems described herein above using exemplary non-parametric models, for example. Further, exemplary embodiments according to the present disclosure can integrate the higher level needs through a relatively simple modification to the score function, for example. Moreover, as one having ordinary skill in the art will appreciate in view of the teachings described herein, it is possible that many of the problems associated with heretofore available technologies do not exist.

Figure 3:
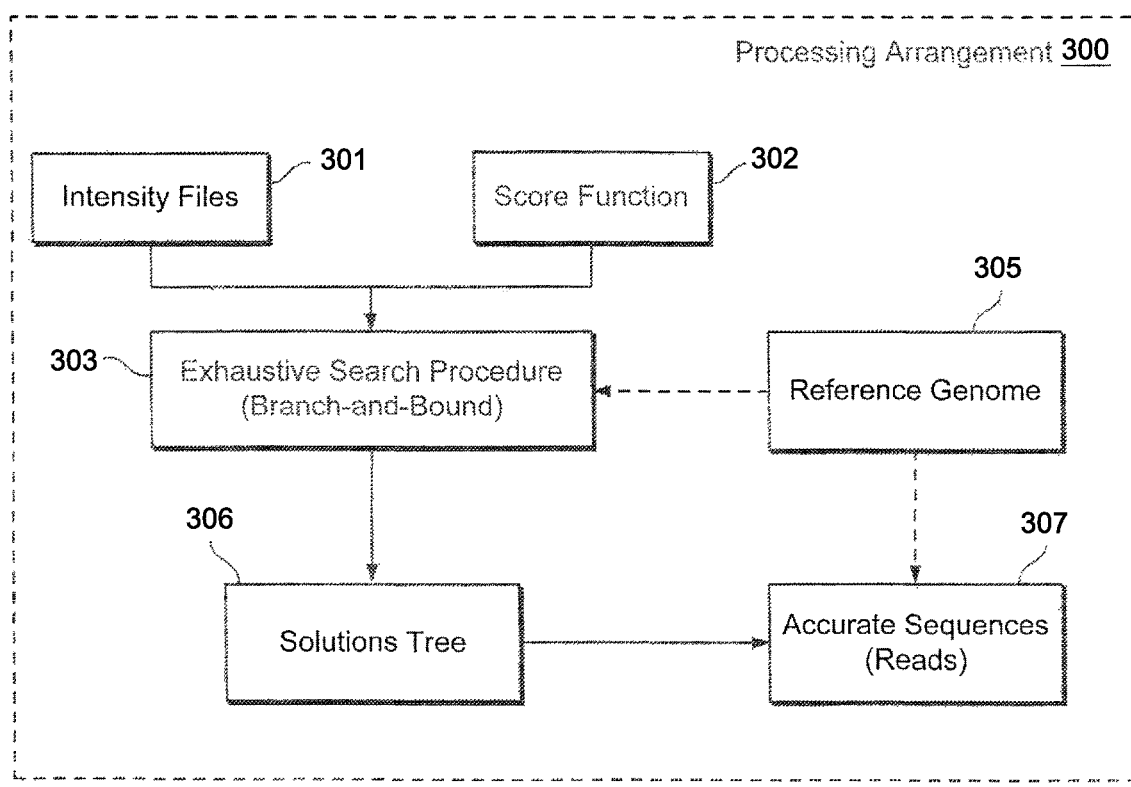
FIG. 3 is an exemplary flow diagram illustrating an exemplary base-caller data flow according to an exemplary embodiment of the present disclosure.

FIG. 3 shows a flow diagram of an exemplary procedure for generating at least one nucleotide sequence in accordance with certain exemplary embodiments of the present disclosure. The exemplary flow chart illustrated in FIG. 3 1 illustrates a base-caller data flow according to certain exemplary embodiments of the present disclosure.

For example, as illustrated in FIG. 3, with the use of a processing arrangement (or computing arrangement) 300, exemplary intensity files 301 from multiple genomic sequences can be combined with an exemplary score function 302 and input into an exemplary exhaustive search procedure/process 303, which can be and/or include a branch-and-bound process in accordance with certain exemplary embodiments of the present disclosure. Input from one or more reference genomes 305 can be used in the exemplary exhaustive search procedure/process 303. Output from the exemplary exhaustive search procedure/process 303 can be provided to an exemplary solutions tree 306. In accordance with certain exemplary embodiments of the present disclosure, accurate sequences (reads) 307 can be achieved (e.g., performed utilizing the processing arrangement 301) using information from the exemplary solutions tree 306. As further illustrated in FIG. 3, it is possible to also use input from the reference genome 305 to achieve and/or perform exemplary accurate sequences (or reads) 307 in accordance with certain exemplary embodiments of the present disclosure.

Figure 4:
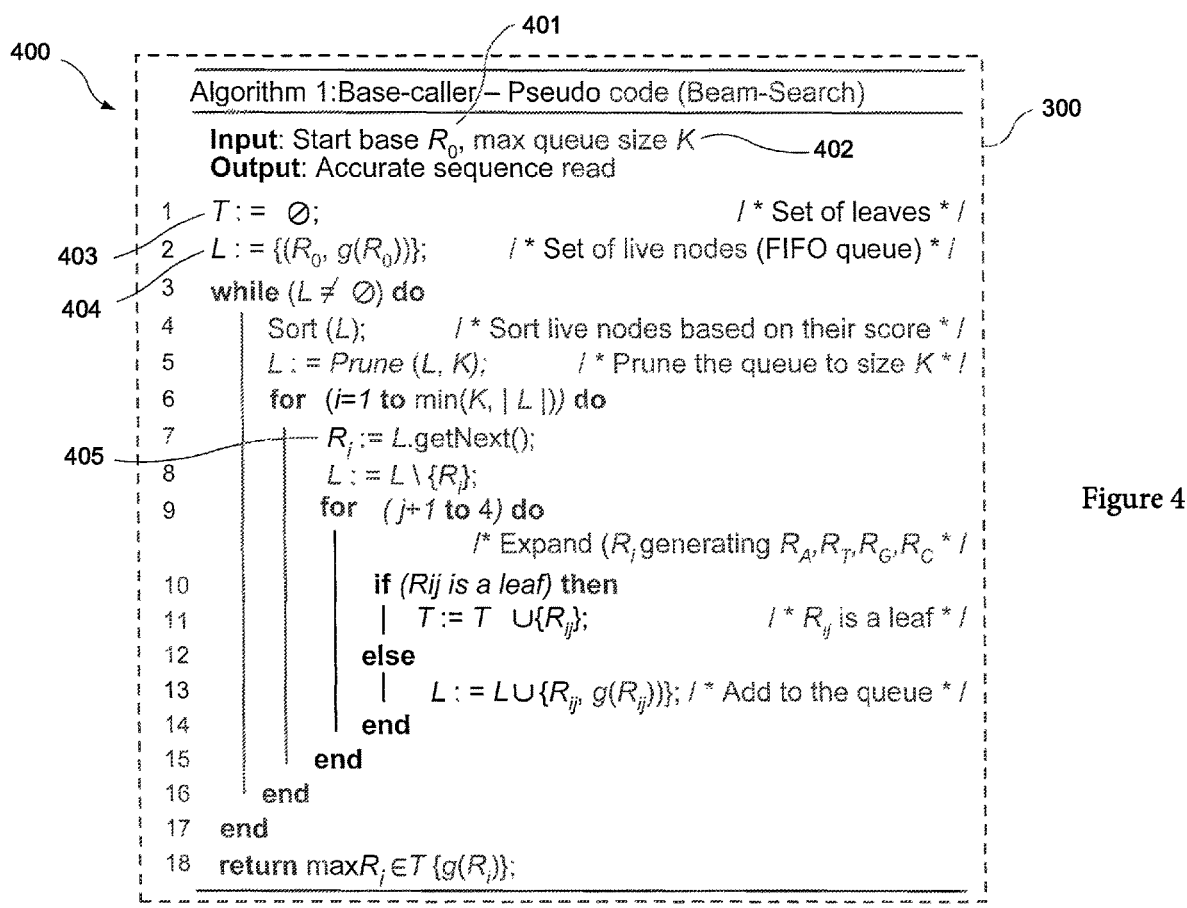
FIG. 4 is an illustration of exemplary base-caller pseudo computer code using an exemplary beam search strategy according to an exemplary embodiment of the present disclosure.

FIG. 4 shows an illustration of exemplary base-caller pseudo computer code using an exemplary beam search strategy in accordance with certain exemplary embodiments of the present disclosure. As illustrated in FIG. 4, exemplary base-caller pseudo computer code 400 can use as input start base $R_0$ 401 and max queue size K 402. As shown in FIG. 4, it is possible to start with a null set of leaves T 403=0, and a set of live nodes $\mathcal{L}$ 404. The set of live nodes $\mathcal{L}$ 404 can include nodes queued in a first in, first out ("FIFO") basis, such that $\mathcal{L} = \{(R_0 \cdot g(R_0))\}$. While the set $\mathcal{L}$ 404 of live nodes is not empty (e.g., $\mathcal{L}$ 404≠0), the exemplary procedure, as implemented by the exemplary base-caller pseudo computer code 400, can sort the set of live nodes $\mathcal{L}$ 404 based on their relative score. This exemplary procedure can then prune the queue to size K 402.

As further shown in FIG. 4, a base $R_i$ 405 can be expanded to generate $R_A \cdot R_T \cdot R_G \cdot R_C$. The exemplary code 400 can then determine whether each resulting base is a leaf. If so, the exemplary computer code 400 can add such to the set of leaves T 403. If not, the node can be added to the queue. This exemplary procedure can be repeated until the set of live nodes $\mathcal{L}$ 404 is equal to zero, upon which an accurate sequence read can be provided/outputted (e.g., displayed and/or stored in a user-accessible format and/or a user-readable format). According to certain exemplary embodiments of the present disclosure, the exemplary computer code 400 can be implemented using a processing/computing arrangement, such as an exemplary processing arrangement 300 of FIG. 3.

Figure 5:
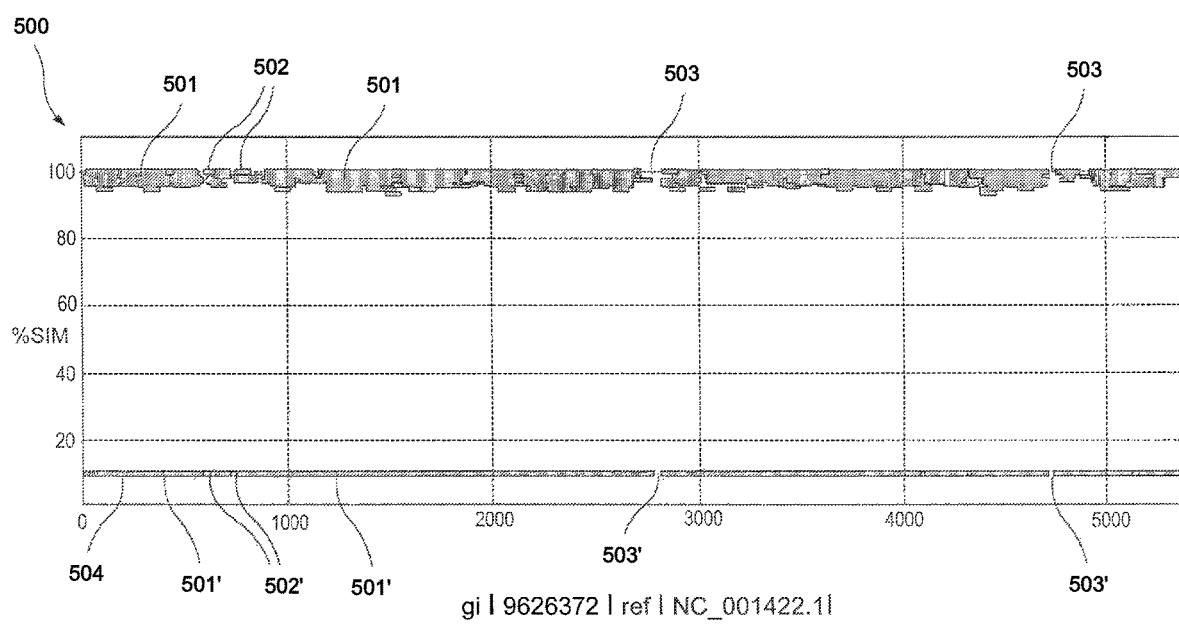
FIG. 5 is a graph of an exemplary percent identity plot according to an exemplary embodiment of the present disclosure.

FIG. 5 shows an exemplary percent identity plot in accordance with certain exemplary embodiments of the present disclosure. As shown in FIG. 5, an exemplary alignment of about 140,000 base-called sequences (reads) of about 78 bases to the phiX reference genome can be depicted. Forward matches 501 can be displayed with reverse matches 502. There are a relatively small number of gaps 503, e.g., in which there are no matches. A corresponding line 504 clearly indicates where there is predominantly forward matches 501, reverse matches 502 and gaps 503, as represented by indications 501', 502' and 503', respectively.

Figure 6:
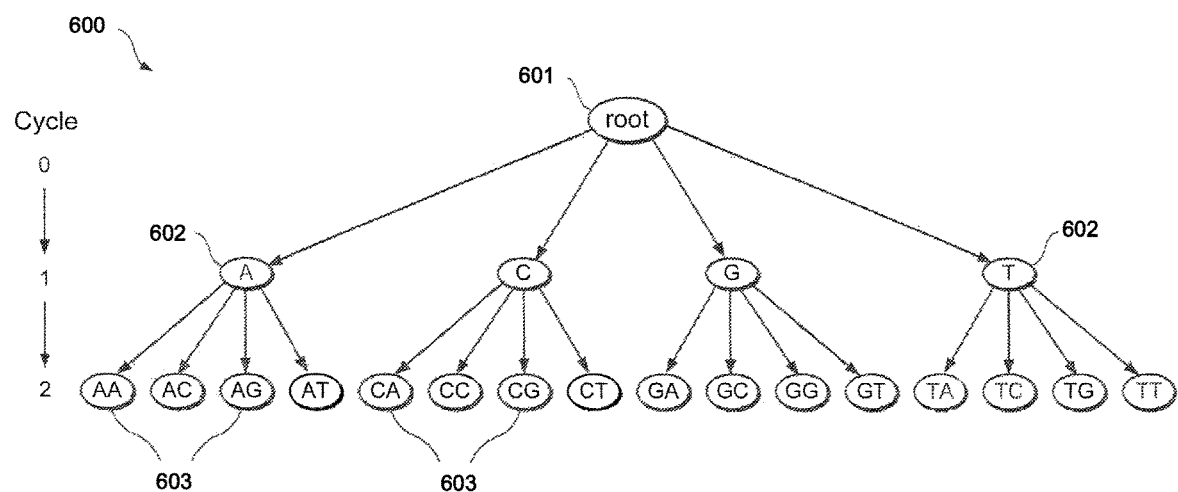
FIG. 6 is a diagram of an exemplary tree that can be generated by an exemplary base-caller procedure according to an exemplary embodiment of the present disclosure.

FIG. 6 shows a diagram of an exemplary tree that can be generated by an exemplary base-caller procedure in accordance with certain exemplary embodiments of the present disclosure. As shown in FIG. 6, an exemplary tree 600 can include root 601 corresponding to cycle 0. The tree 600 can be a quaternary tree (e.g., branching factor=4), where, at each cycle, each node can be expanded by 4, corresponding to A, T, C, and G, for example. Accordingly, in cycle 1, the root 601 can be expanded into four nodes 602. Similarly, in cycle 2, each of the four nodes 602 can be expanded into four nodes 603, resulting in a total of sixteen nodes 603 in cycle 2. The tree 600 can be further expanded in a similar manner in accordance with certain exemplary embodiments of the present disclosure. Further, the tree 600 can be used in, e.g., an exemplary branch-and-bound process, being pruned in accordance with certain exemplary embodiments of the present disclosure, such as shown in FIG. 4 and described herein. For example, it is possible to select all four possible nucleotide bases (e.g., A, T, C, G) of an unexplored leaf node with the best score-value to expand the node by making them its children, computing their respective scores, and repeat the process until the tree 600 cannot be expanded any further.

Figure 7A:
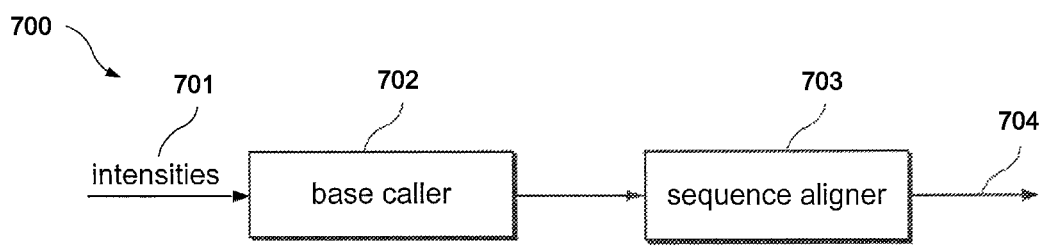
FIG. 7A is an exemplary flow diagram illustrating a traditional resequencing procedure.

FIG. 7A shows an exemplary flow diagram 700 illustrating a traditional resequencing procedure. As shown in FIG. 7A, intensities 701 can be input into a base caller traditional platform 702. The resulting values can then be processed by a sequence aligner 703 to generate output 704.

Figure 7B:
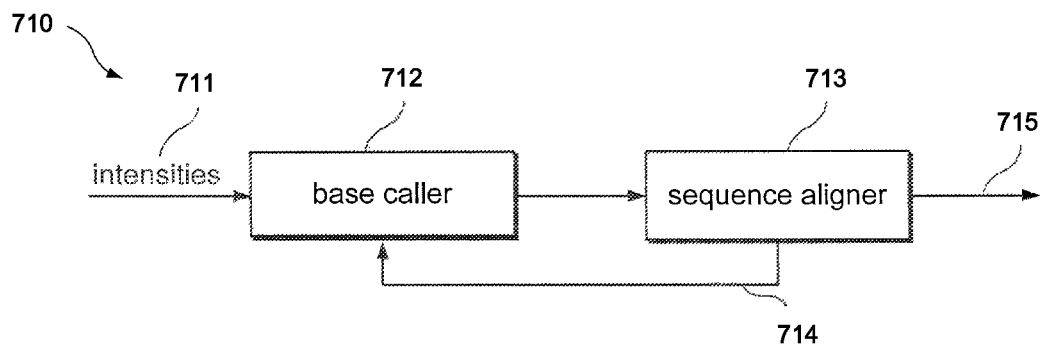
FIG. 7B is an exemplary flow diagram illustrating an exemplary procedure according to an exemplary embodiment of the present disclosure.

FIG. 7B, in contrast, shows an exemplary flow diagram 710 illustrating a procedure in accordance with certain exemplary embodiments of the present disclosure. As shown in FIG. 7B, intensities 711 can be input into an exemplary base-caller 712. The resulting values can then be processed by a sequence an exemplary aligner 713. In contrast to the traditional procedure illustrated in FIG. 7A, the exemplary procedure shown in FIG. 7B can include an exemplary recycle loop 714 to repeat the process, and further refine the values until, e.g., a predetermined threshold level is met, and a preferred level of accuracy is achieved, etc., before generating an output 715.

Figure 8A:
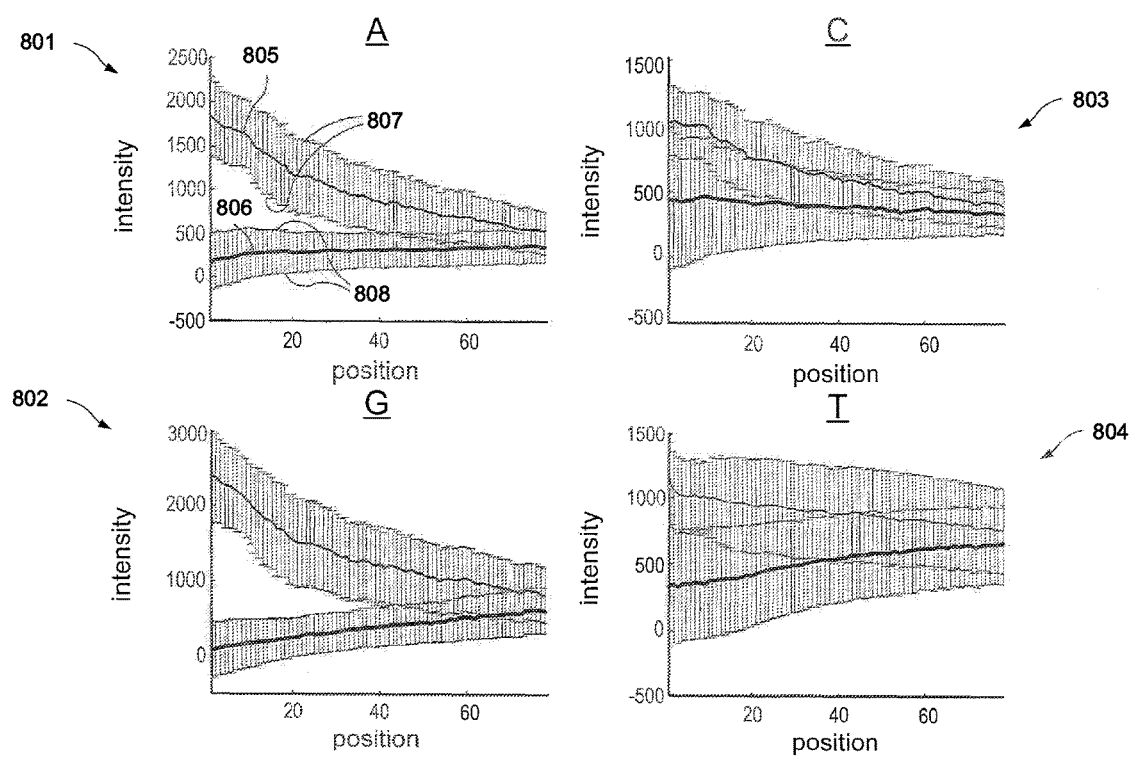
FIG. 8A is an illustration of graphs showing raw intensity values generated by an Illumina technology.

FIG. 8A shows exemplary graphs 801-804 corresponding to nucleotide bases A, C, G, T, respectively, showing raw intensity values generated by an Illumina technology. As shown in FIG. 8A by the labels for mean-averages 805, 806 and corresponding standard deviations 807, 808 of the signals generated by the Illumina technology for each channel, there can be a significant amount of noise associated with the signals associated with these raw intensity values. As described herein above, other previously known technologies likely also generate signals with similar or greater noise levels.

Figure 8B:
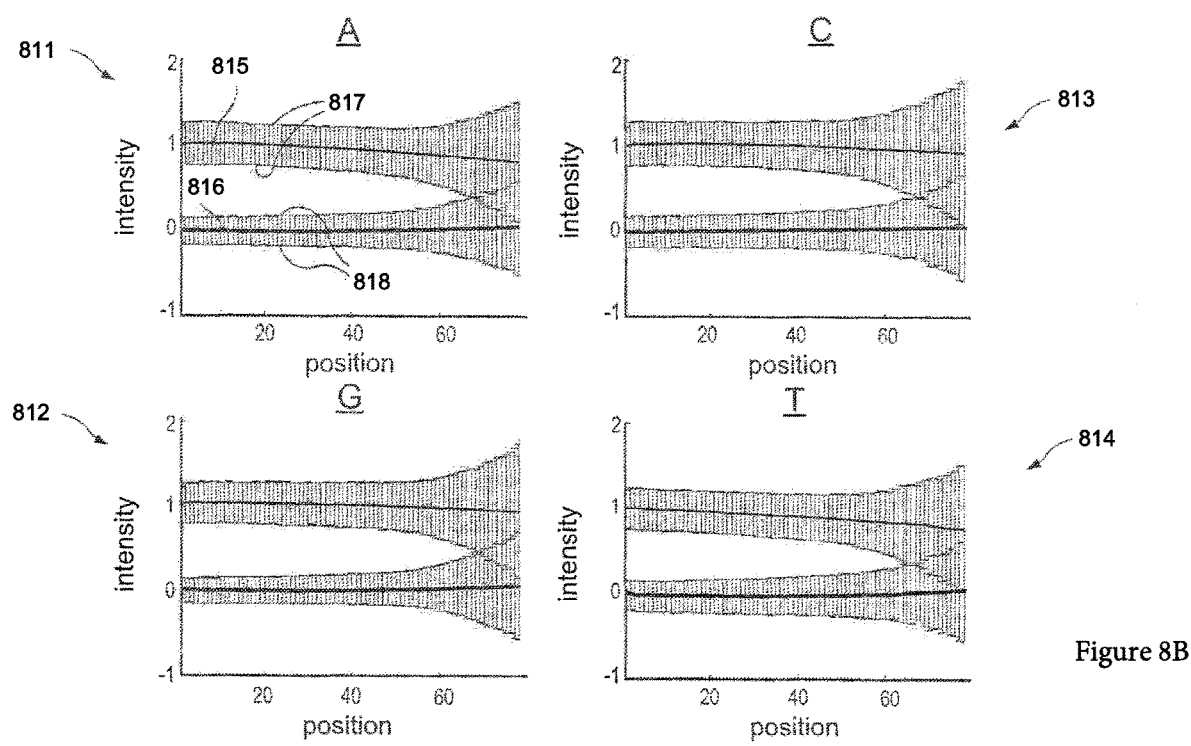
FIG. 8B is an illustration of graphs showing filtered intensity values corresponding to the intensity values of FIG. 8A after being processed by an exemplary procedure according to an exemplary embodiment of the present disclosure.

In contrast, FIG. 8B shows exemplary graphs 811-814 corresponding to nucleotide bases A, C, G, T, respectively, illustrating filtered intensity values corresponding to the intensity values of FIG. 8A after being processed by an exemplary procedure in accordance with certain exemplary embodiments of the present disclosure. As shown in FIG. 8B by the labels for mean-averages 815, 816 and corresponding standard deviations 817, 818, the noise associated with the signals can be reduced using certain exemplary procedures according to the present disclosure described herein (e.g., by the exemplary procedure shown in FIG. 7B and described herein). For example, noise associated with crosstalk and lagging can be reduced by certain exemplary embodiments according to the present disclosure.

Figure 9:
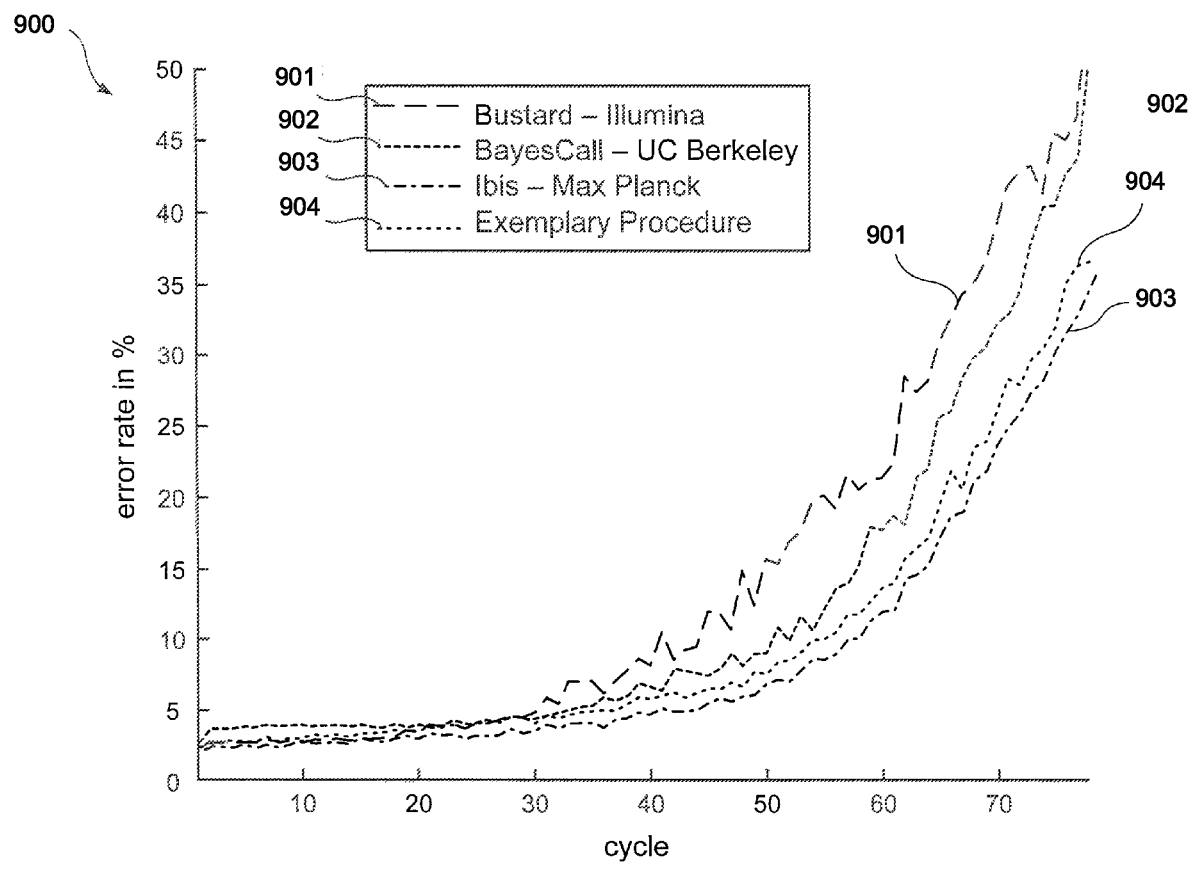
FIG. 9 is a graph showing an exemplary comparison of average error rates by cycle between an exemplary procedure according to an exemplary embodiment of the present disclosure and other base-caller procedures for the phi-x genome.

FIG. 9 shows an exemplary graph 900 illustrating an exemplary comparison of average error rates by cycle between an exemplary procedure in accordance with certain exemplary embodiments of the present disclosure and other base-caller procedures for the phi-x genome. For example, as illustrated in FIG. 9, lines 901-903 can represent error rates associated with certain procedures including Bustard (from Illumina), BayesCall (from University of California, Berkeley) and Ibis (from Max Planck), respectively. Line 904 can represent error rates associated with certain exemplary procedures according to the present disclosure. The error rates 901-904 shown in the graph 900 can be associated with an initial cycle and/or processing for the phi-x genome. As shown, while there can be a similar trend in the error rates between all four procedures, the error rates associated with the initial cycle and/or processing for the phi-x genome of the procedure according to the present disclosure can be more beneficial than the majority of others even without alignment scores being combined in accordance with certain exemplary embodiments of the present disclosure.

Figure 10:
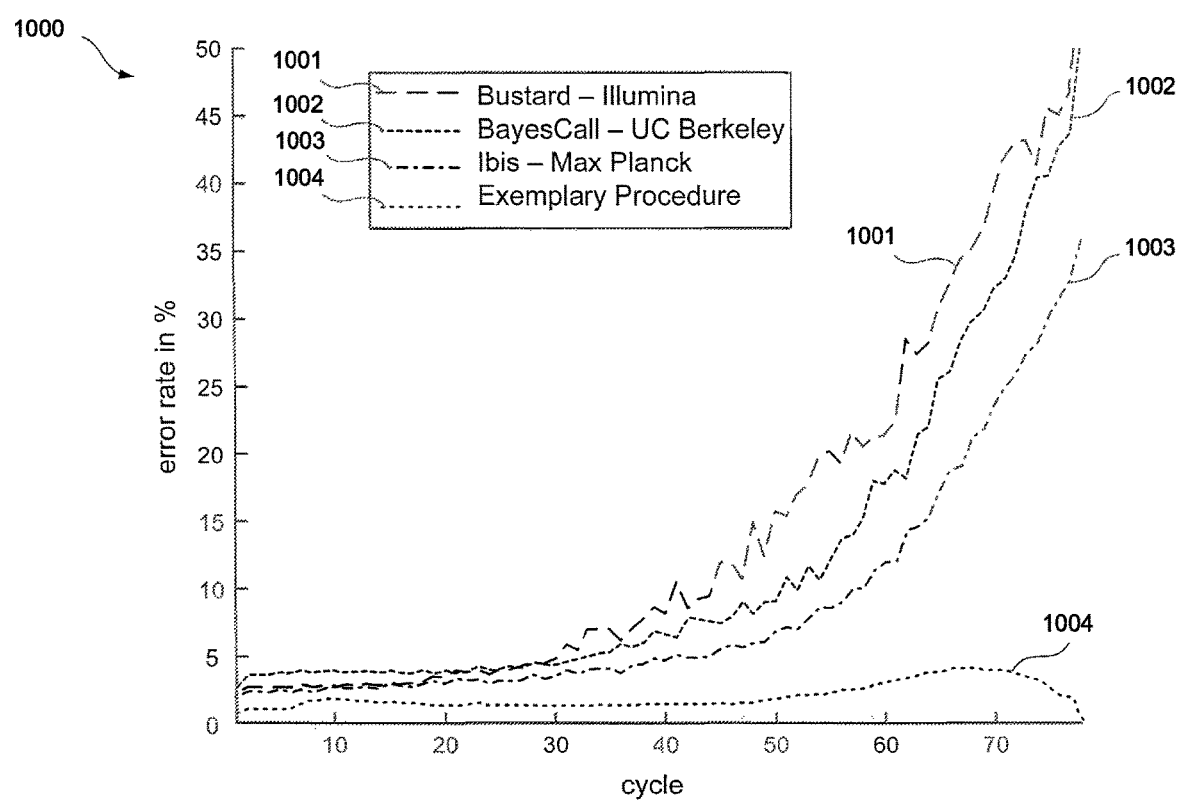
FIG. 10 is a graph showing an exemplary comparison of average error rates by cycle between an exemplary procedure according to an exemplary embodiment of the present disclosure and other base-caller procedures for the phi-x genome with base-calling and alignment scores being combined.

FIG. 10 shows a graph 1000 illustrating an exemplary comparison of average error rates by cycle between the base-caller procedures of FIG. 10 and a procedure in accordance with certain exemplary embodiments of the present disclosure for the phi-x genome with both base-calling and alignment scores being combined according to certain exemplary embodiments of the present disclosure. For example, as shown in FIG. 10, lines 1001-1003 can represent error rates associated with the Bustard (from Illumina), BayesCall (from University of California, Berkeley) and Ibis (from Max Planck) procedures, respectively. The line 1004 can represent error rates associated with certain exemplary procedures according to the present disclosure. As shown in FIG. 10, with the introduction of both base-calling and alignment scores being combined according to certain exemplary embodiments of the present disclosure, the error rates 1004 of the exemplary procedure in accordance with the present disclosure can be significantly reduced, and likely be several times lower than the error rates 1001-1003 associated with the other procedures.

Figure 11:
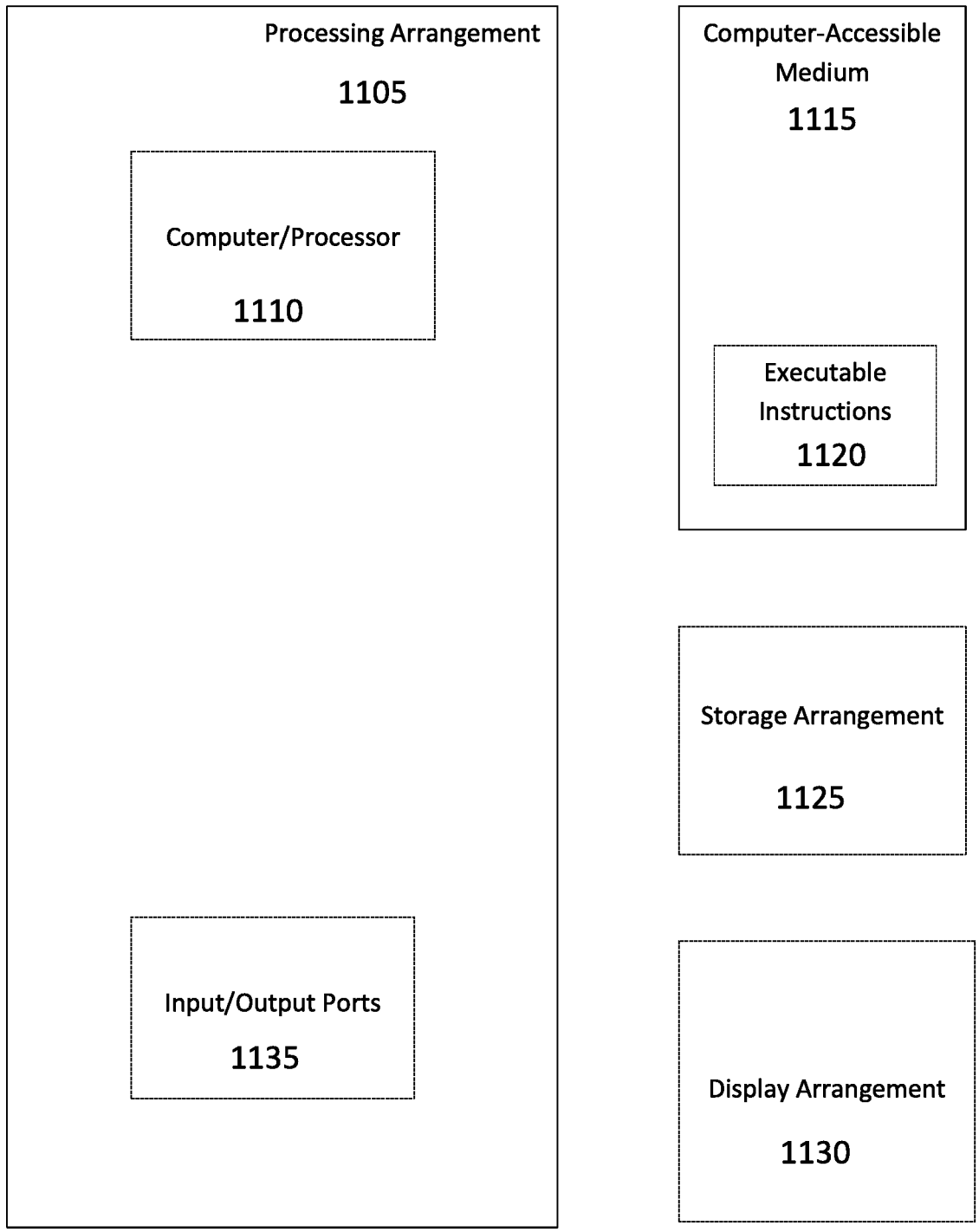
FIG. 11 is an illustration of an exemplary block diagram of an exemplary system in accordance with certain exemplary embodiments of the present disclosure.

As shown in FIG. 11, for example a computer-accessible medium 1115 (e.g., as described herein above, a storage device such as a hard disk, floppy disk, memory stick, CD-ROM, RAM, ROM, etc., or a collection thereof) can be provided (e.g., in communication with the processing arrangement 1105). The computer-accessible medium 1115 can contain executable instructions 1120 thereon. In addition or alternatively, a storage arrangement 1125 can be provided separately from the computer-accessible medium 1115, which can provide the instructions to the processing arrangement 1105 so as to configure the processing arrangement to execute certain exemplary procedures, processes, and methods, as described herein above, for example.

Further, the exemplary processing arrangement 1105 can be provided with or include an input/output ports 1135, which can include, for example a wired network, a wireless network, the internet, an intranet, a data collection probe, a sensor, etc. As shown in FIG. 11, the exemplary processing arrangement 1105 can be in communication with an exemplary display arrangement 1130, which, according to certain exemplary embodiments of the present disclosure, can be a touch-screen configured for inputting information to the processing arrangement in addition to outputting information from the processing arrangement, for example. Further, the exemplary display arrangement 1130 and/or a storage arrangement 1125 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A nucleic acid sequencer comprising a single flow cell and a computer arrangement configured to perform procedures comprising:
   obtain a single raw intensity output derived from a first nucleic acid sequence and a second nucleic acid sequence, wherein the first nucleic acid sequence is in a same flow cell as the second nucleic acid sequence;
   obtain at least one reference sequence for a genome related to the first and second nucleic acid sequence;
   generate and optimize a score function for a plurality of intensities where the score function is configured to determine: (a) that a map path is consistent with one of the first nucleic acid sequence or the second nucleic acid sequence in view of a noise component from another one of the first nucleic acid sequence or the second nucleic acid sequence, and (b) an alignment to the at least one reference sequence, subject to at least one constraint that penalizes the score function based on a fraction of bases that are not consistent with the map path;
   apply the optimized score function to the combined raw intensity output to deconvolve the single raw intensity output into a plurality of constituent intensities;
   map the deconvolved single raw intensity output to a set of possible alignments, the at least one reference sequence and a set of possible base calls; and
   select the first base call and the second base call from the set of possible base calls.

2. The nucleic acid sequencer of claim 1, wherein the combined raw intensity output includes raw intensity outputs received simultaneously from the first and second nucleic acid sequences.

3. The nucleic acid sequencer of claim 1, wherein the combined raw intensity output includes a first raw intensity output received from the first nucleic acid sequence at a first time and a second raw intensity output received from the second nucleic acid sequence at a second time, and wherein the second time is later than the first time.

4. The nucleic acid sequencer of claim 1, wherein the first nucleic acid sequence is the same as the second nucleic acid sequence.

5. The nucleic acid sequencer of claim 1, wherein the first nucleic acid sequence is different than the second nucleic acid sequence.

6. The nucleic acid sequencer of claim 1, wherein the at least one constraint includes at least one penalty function.

7. The nucleic acid sequencer of claim 1, wherein the computer arrangement is further configured to generate the combined raw intensity output by introducing a plurality of primers at different cycles in a Sequencing-By-Synthesis process.

8. The nucleic acid sequencer of claim 1, wherein the computer arrangement is further configured to obtain the at least one reference sequence independently from the combined raw intensity output.

9. The nucleic acid sequencer of claim 8, wherein the set of possible base call includes a first set of possible base calls and a second set of possible base calls, and wherein the computer arrangement is further configured to map the combined raw intensity output to the first set of possible base calls for the first nucleic acid sequence and to the second set of possible base calls for the second nucleic acid sequence.

10. The nucleic acid sequencer of claim 1, wherein the first and second nucleic acid sequences are deoxyribonucleic acid molecules.

11. The nucleic acid sequencer of claim 1, wherein the first and second nucleic acid sequences are ribonucleic acid molecules.

12. The nucleic acid sequencer of claim 1, wherein the at least one reference sequence includes a single reference sequence related to the first and second nucleic acid sequences.

13. The nucleic acid sequencer of claim 1, wherein the at least one reference sequence includes at least two references, and wherein one of the reference sequences is related to the first nucleic acid sequence and another one of the reference sequences is related to the second nucleic acid sequence.

14. The nucleic acid sequencer of claim 1, wherein the computer arrangement is configured to obtain the combined raw intensity from a single channel on the nucleic acid sequencer.

15. The nucleic acid sequencer of claim 1, wherein the computer arrangement is configured to obtain (i) a first raw intensity output of the combined raw intensity output from a first channel on the nucleic acid sequencer, and (ii) a second raw intensity output of the combined raw intensity output from a second channel on the nucleic acid sequencer, and wherein the first channel is different than the second channel.

16. The nucleic acid sequencer of claim 1, wherein the combined raw intensity output includes a first raw intensity output from the first nucleic acid sequence received simultaneously with a second raw intensity output from the second nucleic acid sequence.

17. The nucleic acid sequencer of claim 1, wherein the first and second nucleic acid sequences are from at least one virus.

18. A system for selecting a first base call for a first nucleic acid sequence and a second base call for a second nucleic acid sequence, comprising:
   a nucleic acid sequencer comprising a single flow cell, wherein the nucleic acid sequencer is configured to:
      obtain a single raw intensity output derived from the first nucleic acid sequence and the second nucleic acid sequence, wherein the first nucleic acid sequence is in a same flow cell as the second nucleic acid sequence;
      obtain at least one reference sequence for a genome related to the first and second nucleic acid sequence;
      with the nucleic acid sequencer, generate and optimize a score function, subject to at least one constraint, based on a plurality of intensities and the at least one reference sequence, wherein the score function is configured to determine: (a) that a map path is consistent with one of the first nucleic acid sequence or the second nucleic acid sequence in view of a noise component from another one of the first nucleic acid sequence or the second nucleic acid sequence, and (b) an alignment to the at least one reference sequence, that penalizes the score function based on a fraction of bases that are not consistent with the map;
      apply the optimized score function to the combined raw intensity output;
      map, by the nucleic acid sequencer, the deconvolved single raw intensity output to a set of possible alignments, the at least one reference sequence and a set of possible base calls; and select the first base call and the second base call from the set of possible base calls.

19. A method for selecting a first base call for a first nucleic acid sequence and a second base call for a second nucleic acid sequence, comprising:

obtaining, via a nucleic acid sequencer with a single flow cell, a single raw intensity output derived from the first nucleic acid sequence and the second nucleic acid sequence, wherein the first nucleic acid sequence is in a same flow cell as the second nucleic acid sequence;

obtaining at least one reference sequence for a genome related to the first and second nucleic acid sequence;

with the nucleic acid sequencer, generating and optimizing a score function, for a plurality of intensities where the score function is configured to determine: (a) that a map path is consistent with one of the first nucleic acid sequence or the second nucleic acid sequence in view of a noise component from another one of the first nucleic acid sequence or the second nucleic acid sequence, and (b) an alignment to the at least one reference sequence, that penalizes the score function based on a fraction of bases that are not consistent with the map path;

applying the optimized score function to the combined raw intensity output to deconvolve the single raw intensity output into a plurality of constituent intensities;

mapping, by the nucleic acid sequencer, the deconvolved single raw intensity output to a set of possible alignments, the at least one reference sequence and a set of possible base calls; and selecting, by the nucleic acid sequencer, the first base call and the second base call from the set of possible base calls.

20. The method of claim 19, further comprising:

placing the first and second nucleic acid molecules on a single flow cell; and inserting the single flow cell into the nucleic acid sequencer with a single flow cell.

* * * * *